United States Patent
Yufa

[11] Patent Number: 6,034,769
[45] Date of Patent: *Mar. 7, 2000

[54] METHOD AND DEVICE FOR COUNTING AND MEASURING PARTICLES

[76] Inventor: Aleksandr L. Yufa, P.O. Box 1677, Colton, Calif. 92324

[*] Notice: This patent issued on a continued prosecution application filed under 37 CFR 1.53(d), and is subject to the twenty year patent term provisions of 35 U.S.C. 154(a)(2).

[21] Appl. No.: 08/884,680

[22] Filed: Jun. 27, 1997

[51] Int. Cl.⁷ ................................. G01N 15/02
[52] U.S. Cl. .................. 356/335; 356/336; 356/339; 377/11
[58] Field of Search ................. 356/335–343, 356/436, 433, 435; 250/573, 576, 577; 377/10, 11

[56] References Cited

U.S. PATENT DOCUMENTS

| | | | |
|---|---|---|---|
| 3,591,290 | 7/1971 | Zinner | 356/335 |
| 4,595,291 | 6/1986 | Tatsuno | 356/336 |
| 5,059,395 | 10/1991 | Brittenham et al. | 356/335 |
| 5,325,169 | 6/1994 | Nakamoto et al. | 356/336 |
| 5,610,712 | 3/1997 | Schmitz et al. | 356/343 |
| 5,619,333 | 4/1997 | Staff et al. | 356/335 |
| 5,731,875 | 3/1998 | Chandler et al. | 356/336 |

*Primary Examiner*—Hoa Q. Pham

[57] ABSTRACT

A device for counting and measuring particles provides an analysis of the particle characteristics and includes a processing system 27, comprising a control subsystem 13, including a microprocessor subsystem 20 and a terminal devices 21, an analog-digital subsystem 14, comprising an amplifier 15 and a pulse former 24, and a light detecting system 11, providing particle detection. An improved device determines the size of particles by the quantity of the strobe pulses of the strobe pulse sequence within each strobe pulse pack, formed from the amplified and converted output of the light detecting system 11. The quantity of the identical strobe pulse packs characterizes the quantity of the particles with an appropriate identical size.

6 Claims, 10 Drawing Sheets

METHOD AND DEVICE FOR COUNTING AND MEASURING PARTICLES

FIELD OF THE INVENTION

This invention relates to air and liquid quality and, more particularly, to devices and instruments for particle quantity counting and particle size measuring by light or laser beam.

BACKGROUND OF THE INVENTION

The methods and devices for determining quantity and size of the particles and small bodies are now well known, and it is also well known that powerful light or laser and optical system or mirror can be, and have been, heretofore used to achieve particle size and particle quantity measurements. Such devices are well known and described in the articles: R. G. Knollenberg, B. Schuster—"Detection and Sizing of Small Particles in Open Cavity Gas Laser," Applied Optics, Vo.11, No.7, November 1972, pp.1515–1520; R. G. Knollenberg—"An Active Scattering Aerosol Spectrometer," Atmospheric Technology, No.2. June 1973, pp.80–81; Schehl, Ergun, Headrick—"Size Spectrometry of Aerosols Using Light Scattering from the Cavity of a Gas Laser," Review of Scientific Instruments, Vol. 44, No. 9, September 1973; R. G. Knollenberg—"Active Scattering Aerosol Spectrometry," National Bureau of Standards Special Publication, No.412, October 1974, pp.57–64; R. G. Knollenberg, R. E. Luehr—"Open Cavity Laser Active Scattering Particle Spectrometry from 0.05 to 5.0 Microns," Fine Particles, Aerosol Generation Measurement, Sampling and Analysis, Academic Press, May 1975, pp.669–696; R. G. Knollenberg—"Three New Instruments for Cloud Physics Measurements: The 2-D Spectrometer, the Forward Scattering Spectrometer Probe, and the Active Scattering Aerosol Spectrometer", American Meteorological Society, International Conference on Cloud Physics, July 1976, pp. 554–561; R. G. Knollenberg—"The Use of Low Power Laser in Particle Size Spectrometry", Proceeding of the Society of Photo-Optical Instrumentation Engineers, Practical Applications of Low Power Lasers, Vo.92, August 1976, pp.137–152; Elterman—"Brewster Angle Light Trap," Applied Optics, Vol. 16, No. 9, September 1977; Marple—"The Aerodynamics Size Calibration of Optical Particle Counters by Inertial Impactors," Aerosol Measurement 1979; Diehl, Smith, Sydor—"Analysis by Suspended Solids by Single-Particle Scattering," Applied Optics, Vol. 18, No. 10, May 1979; K. Suda—Review of Scientific Instruments, Vol. 51, No. 8, August 1980, pp.1049–1058; R. G. Knollenberg—"The Measurement of Particle Sizes Below 0.1 Micrometers", Journal of Environment Science, January–February, 1985, pp. 64–67; Peters—"20 Good Reasons to Use In Situ Particle Monitors", Semiconductor International, Nov. 1992, pp.52–57 and Busselman et al.—"In Situ Particle Monitoring in a Single Wafer Poly Silicon and Silicon Nitride Etch System", IEEE/SEMI Int'l Semiconductor Manufacturing Science Symposium, 1993, pp.20–26.

The reference in these articles is made to the devices and methods of particle measurement utilizing an open cavity laser. These methods and devices use imaging systems, which are based on lens use, the same as it mentioned, for example, in U.S. Pat. No. 4,140,395, U.S. Pat. No. 4,798, 465 and in U.S. Pat. No. 5,495,105 of the prior art.

The other devices mentioned in prior art (for example, U.S. Pat. No. 4,606,636) use a non-divergent quadric reflector. Such devices use a paraboloidal sphere as mirror.

Yet in other prior art (for example, such as U.S. Pat. No. 4,189,236, U.S. Pat. No. 4,523,841, U.S. Pat. No. 5,467,189 and U.S. Pat. No. 5,515,164) we can find the devices (sensors) with ellipsoidal mirrors instead of the lens systems or non-divergent quadric mirrors.

All these devices, mentioned in the prior art above, use light scattering focalizing methods. Such methods are based on the collection of the scattered light. A light scattering occurs at the first focal point (focus) by particles in the laser beam. Considering stochastic dispersion of the scattered light, the devices, mentioned in the above prior art, use mirrors or optics. This is necessary for scattered light collecting and focalizing at the second focal point (focus), where a light detector is placed and intended for scattered light detection.

Another known method uses direct detection, as it mentioned in U.S. Pat. No. 5,085,500. By this method, the scattered light in such devices is detected by the light detectors directly with no scattered light collection.

As shown on FIG. 1, related to the use of the optics, regarding the U.S. Pat. No. 4,140,395, No. 4,798,465, and No. 5,495,105, the scattered light 6 is collected by the optical system 10, which is presented by the lenses.

On FIG. 2 is presented the device, using non-divergent quadric mirror, (U.S. Pat. No. 4,606,636). From FIG. 2 we see that the collection of the scattered light is provided by non-divergent quadric mirror 18.

The counting and measuring devices (sensors), mentioned in the U.S. Pat. No. 4,189,236, No. 4,523,841, No. 5,467, 189, and No. 5,471,299, using an ellipsoidal mirrors 17, are presented on simplified FIG. 3.

On FIG. 4 is presented the particle sensor by U.S. Pat. No. 5,515,164, also using the ellipsoidal mirror for the scattered light collection. This sensor uses specially increased cross-section outlet area of the particle flow.

On FIG. 5 is shown a simplified drawing of the device, using the direct detection method.

It is understood, that the methods and devices, mentioned of the prior art of the above, require the use of the scattered light collection means and systems (FIGS. 1–4) or very large spatial surface of the light detector or sufficient quantity of the light detectors (FIG. 5). Such methods and/or devices need to include expensive means and systems. Also, the mentioned above methods and devices have a common deficiency, which is characterized by non-consideration of all scattered light plurality (for example, a scattered light 23 on FIGS. 1–5) and non-precise focalizing of the particle flow (for example, a scattered light 7 on FIGS. 1–5).

It is known, that integrated circuits (chips) and semiconductors have been produced in "clean rooms". The air in such "clean rooms" should be very well cleaned. The continuing tendencies of improvement in circuit integration and degree of microminiaturization require corresponding improvements of the environment in "clean rooms" and efficiency of the measuring devices. And now, as known from prior art, the sensitivity of the counting and measuring devices should be at least as small as 0.1 $\mu$m (Micron). Some known devices (for example, by U.S. Pat. No. 5,731,875) use a plurality of light emitting lasers intended for the power decreasing, that provides the elimination of the laser heat-sink, but, it requires to use a plurality of fiber optic stands and the optical element(s) for the focusing of a plurality of light beams.

Thus, the unfocused and/or unconsidered (undetected) scattered light in the mentioned above devices of a prior art creates light background (light noises) inside such devices, creating thereby incorrectness of the resulting information about the measured environment. Additionally, such light noises limit the sensitivity of such devices.

Also the devices, based on scattered light collection and some other detection methods (for example, by light splitting), use a different variations of the analog comparison method for the particle counting and measuring. Such methods can be illustrated, for example, by U.S. Pat. No. 4,798,465, wherein is shown the particle size detection device, using one of the particle measuring comparison method variation. The signals from detectors via the amplifiers follow to the comparators, which are connected to the reference voltage means. The amplified detected signal is compared with the predetermined reference voltage for the particle size qualifying.

Such analog methods cannot provide a sufficiently high sensitivity related to the increasing environmental requirements, because of the non-precise analog method of comparison.

OBJECT AND ADVANTAGES OF THE INVENTION

Accordingly, several objects and advantages of the present invention are to provide an improved method and device for counting and measuring particles.

It is another object of the invention to provide an improved method and device for increasing the precision of particle counting and measuring.

It is still another object of the invention to provide an improved method and device for increasing the efficiency of the measuring and counting process.

It is still further an object of the invention to provide an improved method and device for increasing the authenticity of the information about air or liquid composition.

It is yet another object of the invention to provide an improved method and device for decreasing light noises by the elimination of unfocused and/or unconsidered scattered light.

It is another further object of the invention to provide an improved method and device for increasing sensitivity of the particle size detection by the elimination of the scattered light collection. It is yet further object of the invention to provide an improved method and device for substantial decreasing of the light (laser) power source.

Still, further objects and advantages will become apparent from a consideration of the ensuing description accompanying drawings.

SUMMARY OF THE INVENTION

The invention provides a method and device, having a high sensitivity and a precision of counting and measuring particles, wherein a particle size sensitivity achieves at least as small as 0.1 $\mu$m. An improved method of counting and measuring particles forms direct detection processes, eliminating the light scattering detection principles. An improved device, realizing the improved direct detection method, includes a light detecting system and a processing system, including an analog-digital subsystem and a control subsystem. A light or laser beam intersects a particle flow inside a light detecting system in the light detection means area. The light detection means is placed on the light beam axis. The signals, detected by light detection means through an analog-digital subsystem follow to a processing system for signal processing and information displaying. The improved method and device provide the direct detection of the particles and timing processing of the detected signals.

By an improved method, the improved timing processing of the detected signals is provided by strobing of the digital form pulses, created from the appropriate amplified detected signals and having the different durations created by appropriate different size particles, intersecting the light beam.

DESCRIPTION OF THE PREFERRED EMBODIMENTS

Here the description of an improved method and device will be done in statics (as if the components of the improved device are suspended in the space) with description of their relative locations and connections to each other. The description of the improved processes and functional operations of an improved device will be done hereafter.

Figure 1:
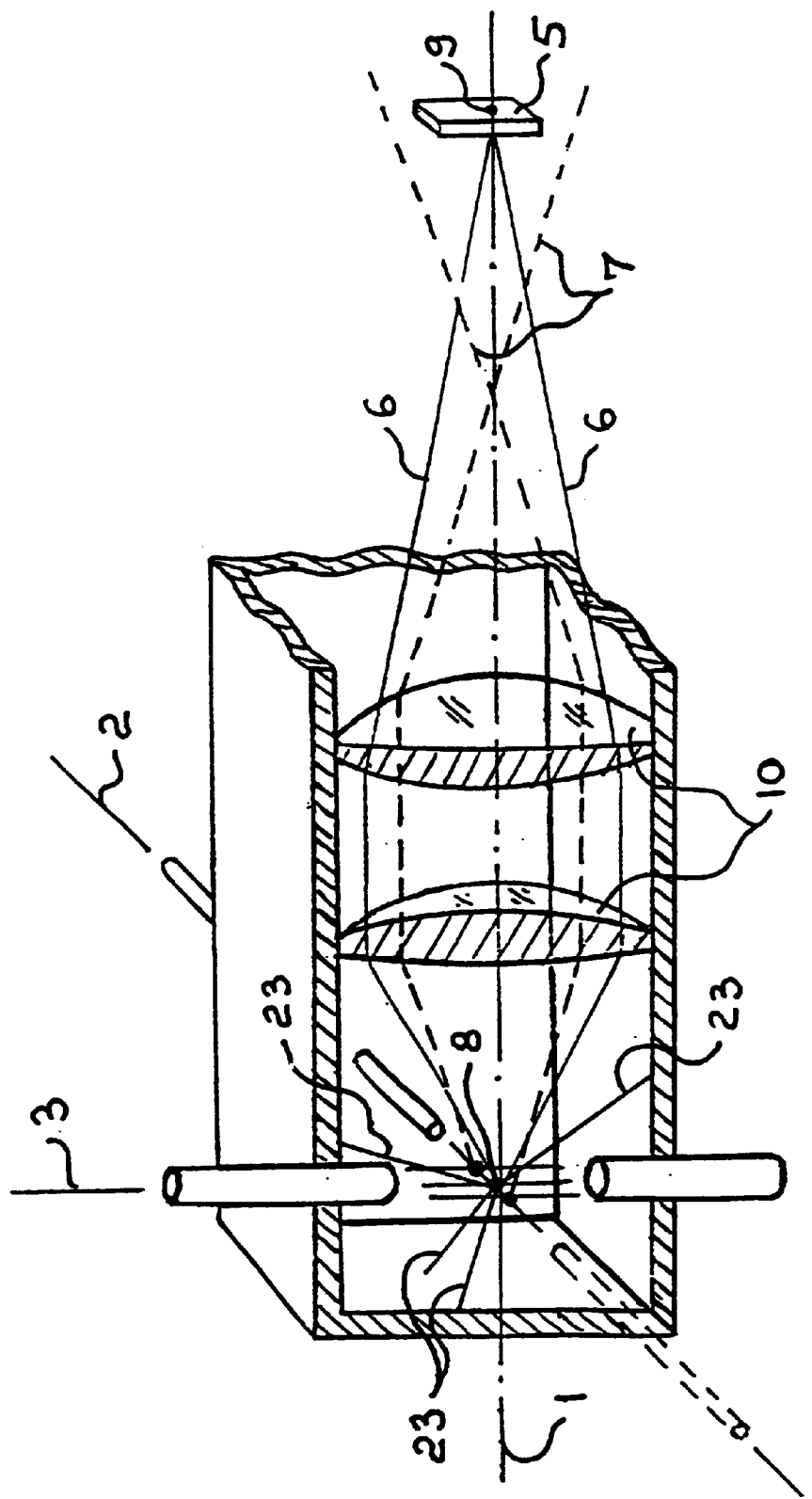
FIG. 1 is a presentation of the scattered light collection by an optics in the prior art.
Figure 2:
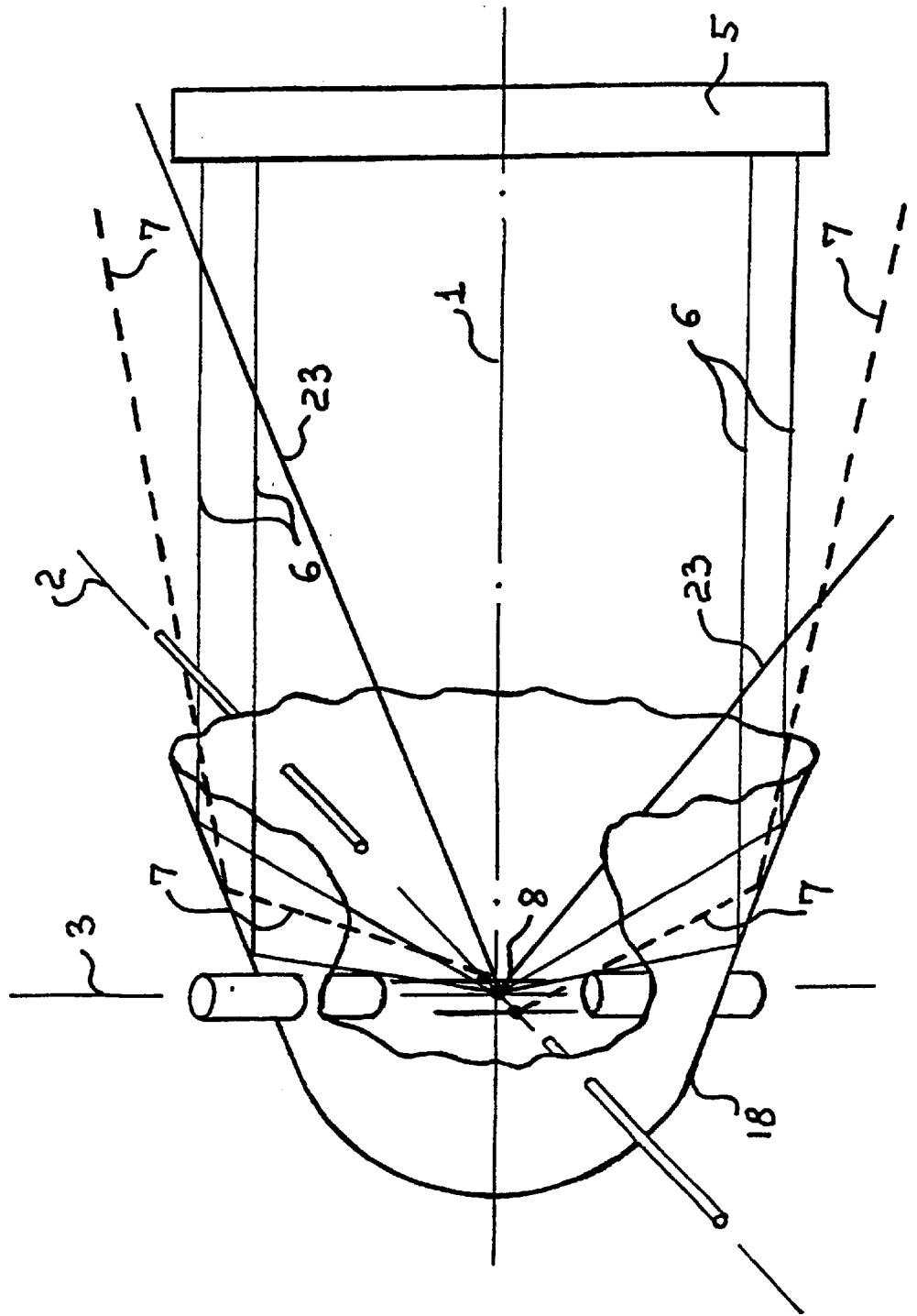
FIG. 2 is a presentation of the scattered light collection by a non-divergent quadric mirror in the prior art.
Figure 3:
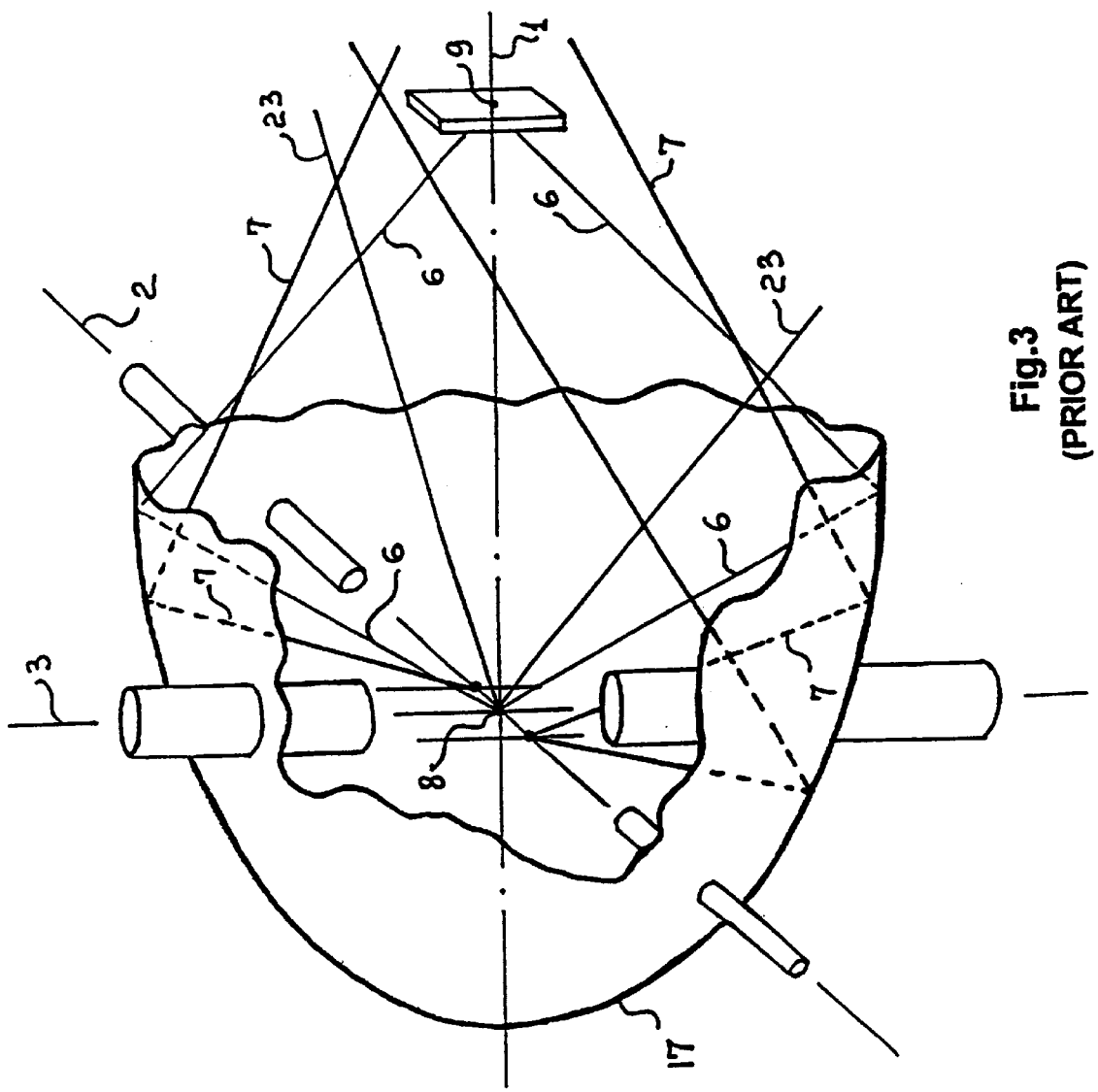
FIG. 3 is a presentation of the scattered light collection by an ellipsoidal mirror in the prior art.
Figure 4:
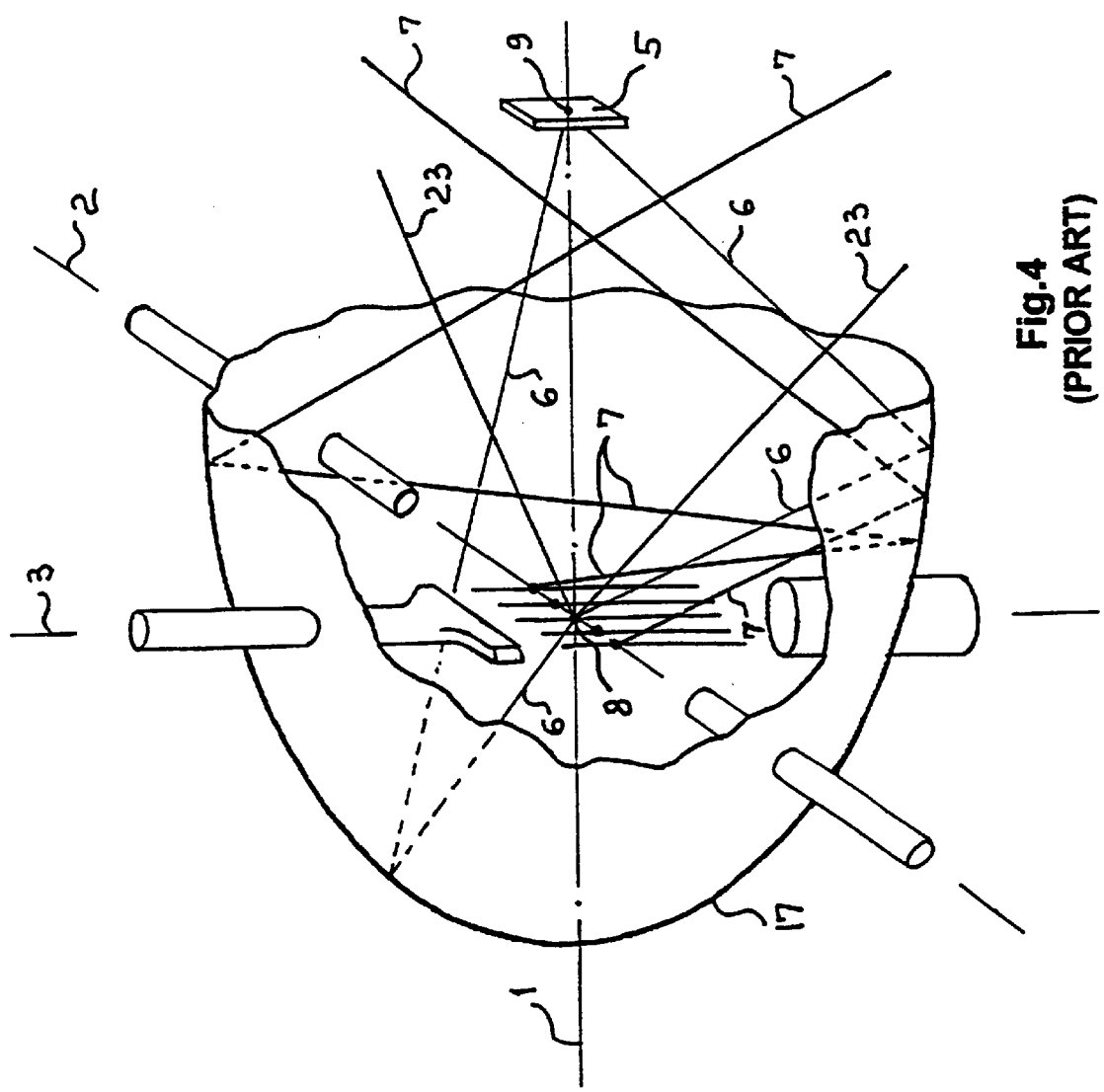
FIG. 4 is a presentation of the scattered light collection by an ellipsoidal mirror with the especially increased inlet cross-sectional area of the particle flow in the prior art.
Figure 5:
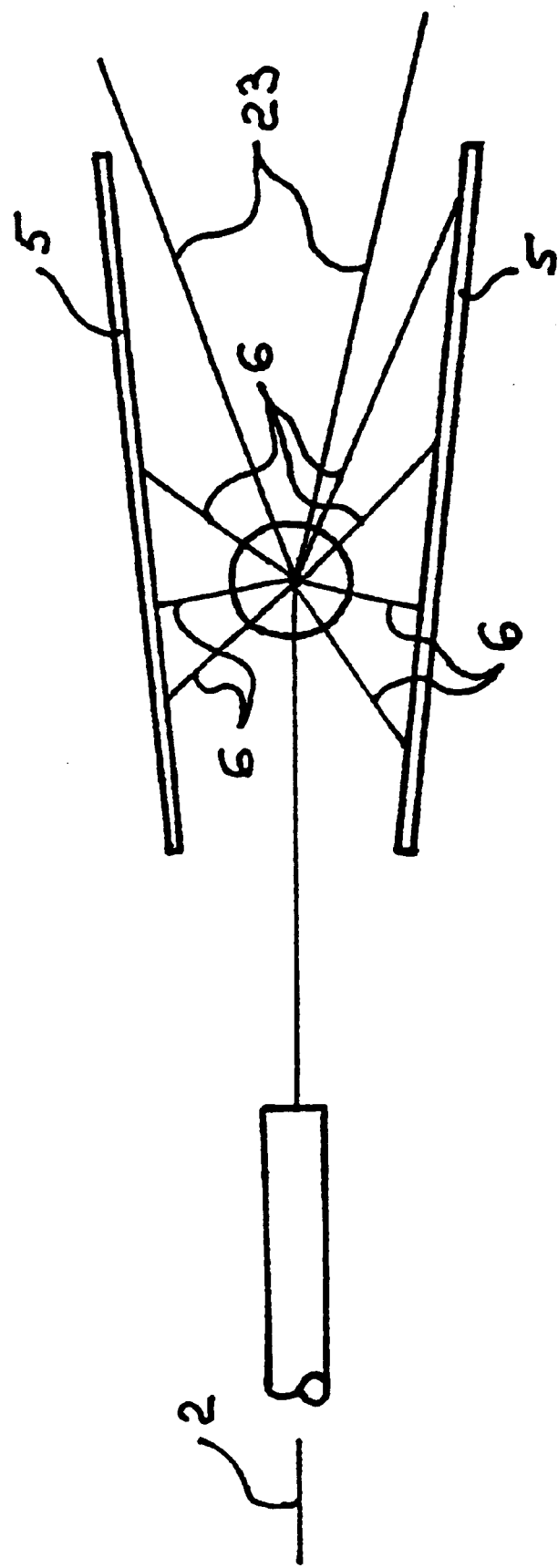
FIG. 5 is a presentation of the scattered light direct detection method in the prior art.
Figure 6:
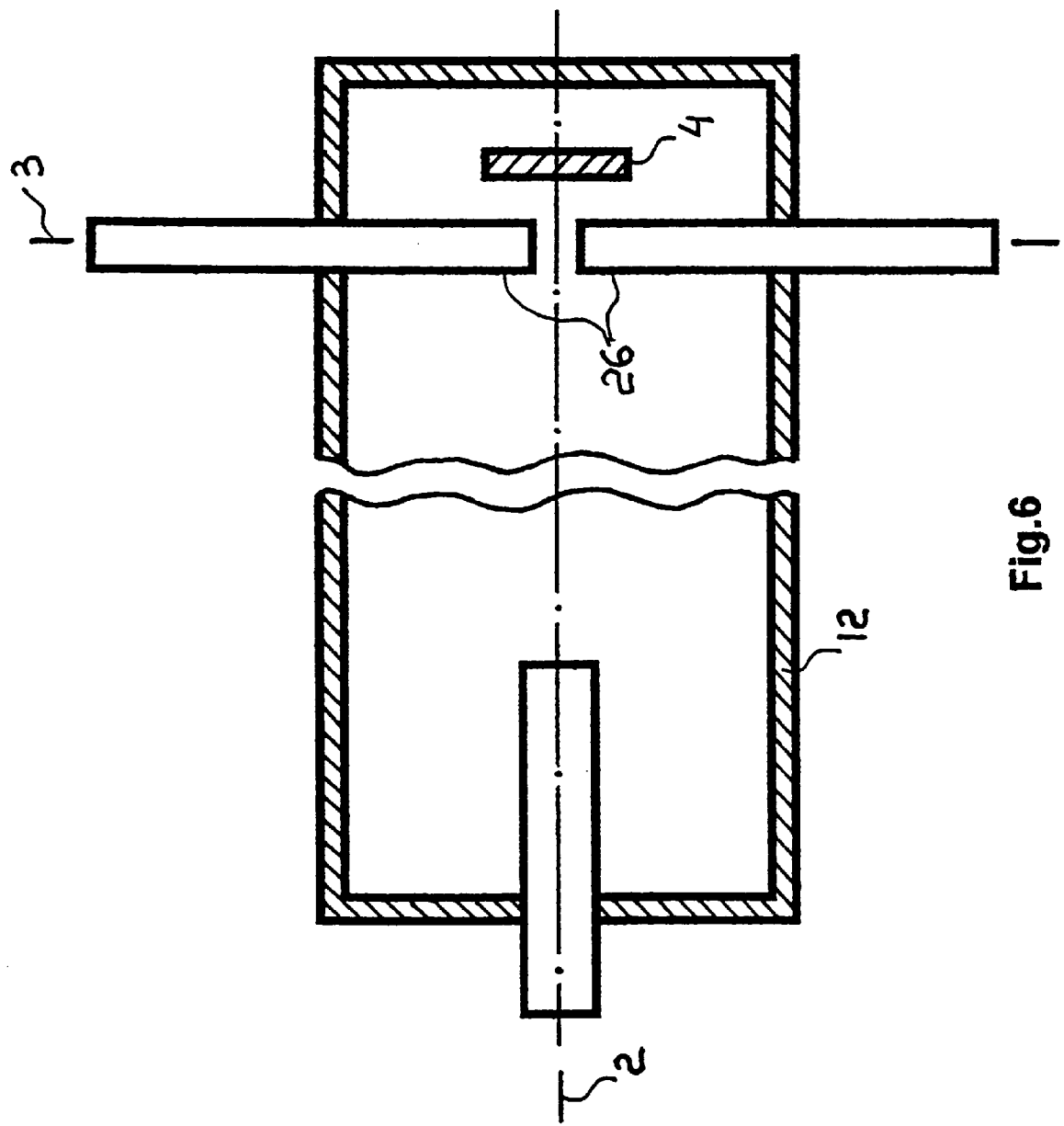
FIG. 6 is a presentation of the simplified drawing of the light detecting system of the improved device with the divided particle flow tubular means.
Figure 7:
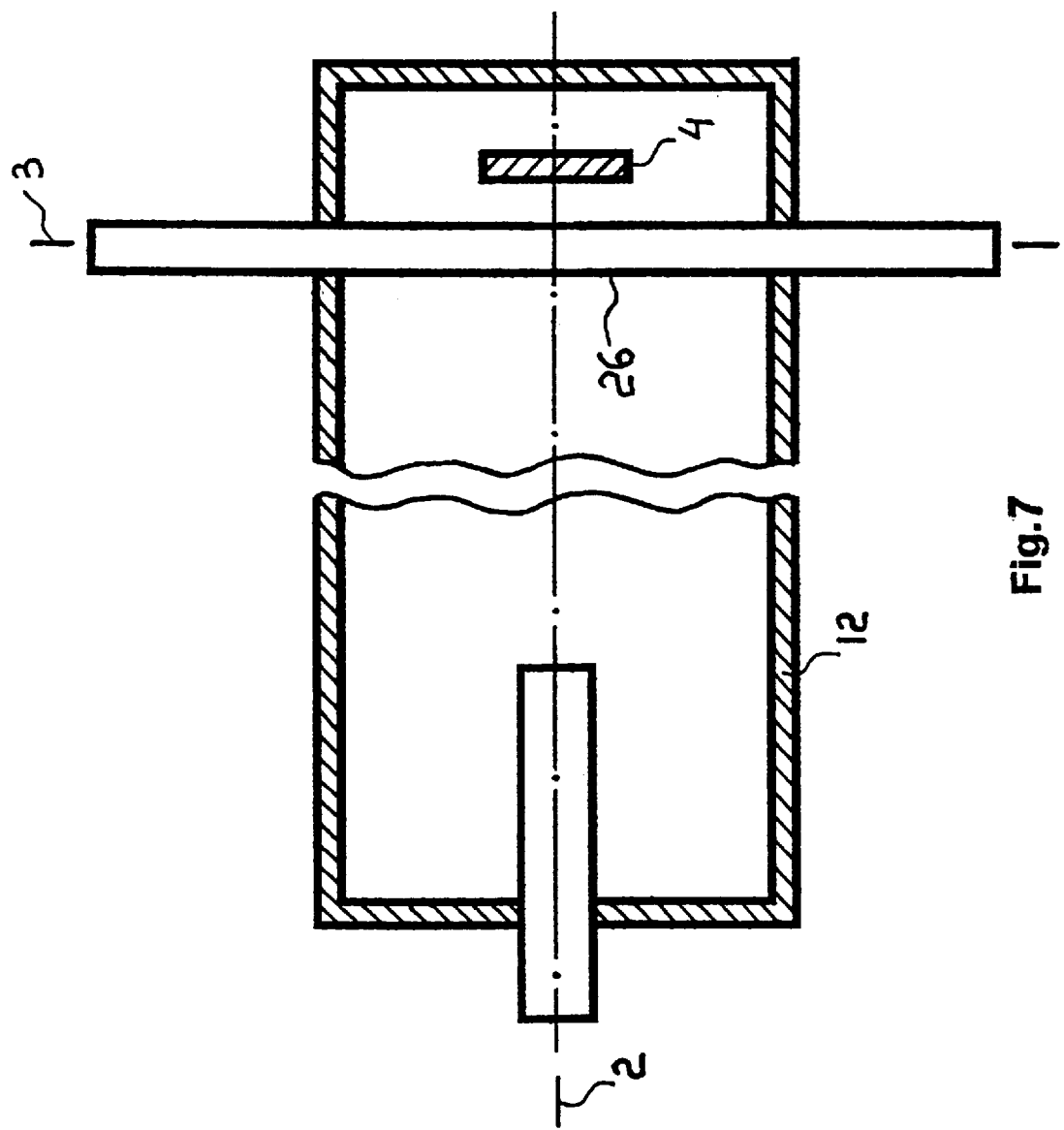
FIG. 7 is presentation of the simplified drawing of the light detecting system of the improved device with non-divided particle flow tubular means.

Referring to FIGS. 6, 7, a light detecting system 11 includes a chamber 12, a light beam axis 2 (a laser beam can be used), a particle flow along axis 3, light detection means 4 and a particle flow tubular means 26. For example the particle flow tubular (capillary) means 26, intended for airborne particle passage, can be divided (interrupted) in the light detection means 4 area for the inlet particle flow tubular means and outlet particle flow tubular means (see FIG. 6). A chamber 12 of the light detecting system 11 has a black flat (rough) inside coating, absorbing possible reflected light and eliminating thereby possible light background (light noises).

Figure 8:
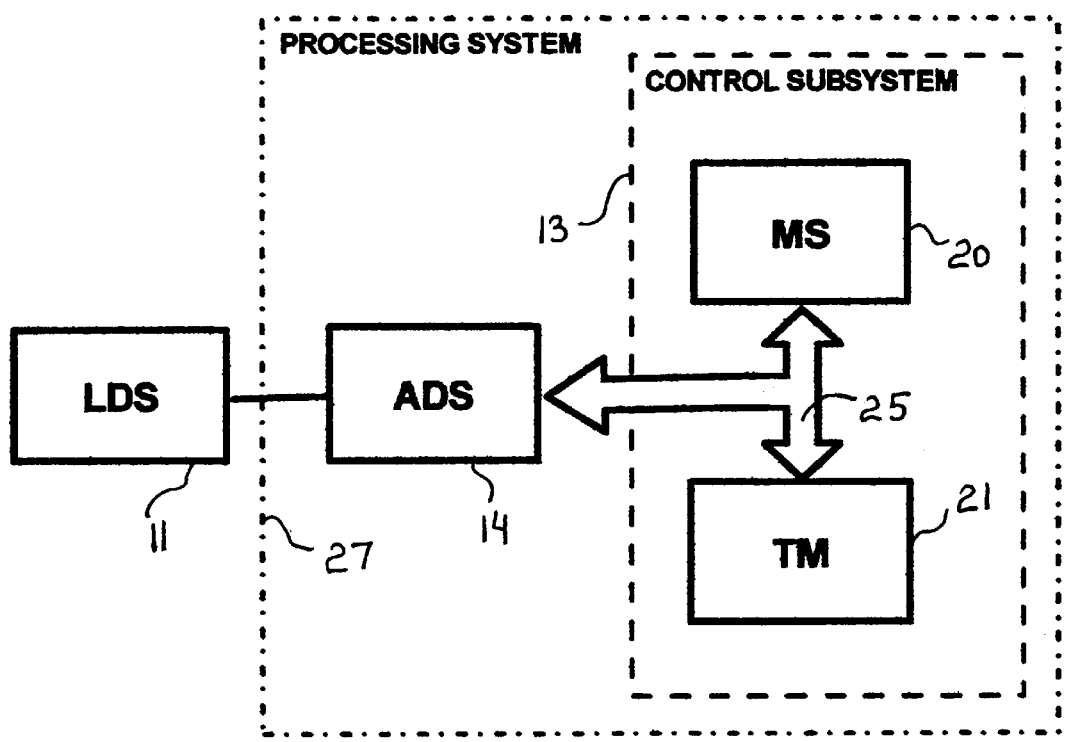
FIG. 8 is a presentation of the block diagram of an improved device.

On FIG. 8 is shown a simplified presentation of an improved device, including a light detecting system 11, connected to an analog-digital subsystem 14 of a processing system 27. The analog-digital subsystem 14 is by a multiplexed bus 25 connected to a control subsystem 13 of a processing system 27. The control subsystem 13 includes a microprocessor subsystem 20 and a terminal means 21.

Figure 9:
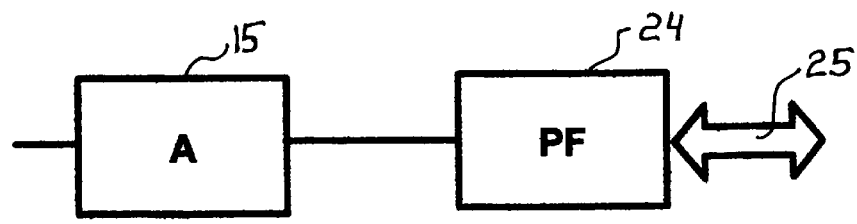
FIG. 9 is a presentation of the block-diagram of the analog-digital subsystem of an improved device.

On FIG. 9 is presented an analog-digital subsystem, realizing a time processing of the detected light signals. Mentioned analog-digital subsystem comprises an amplifying means 15, connected to a pulse forming means 24.

Figure 10:
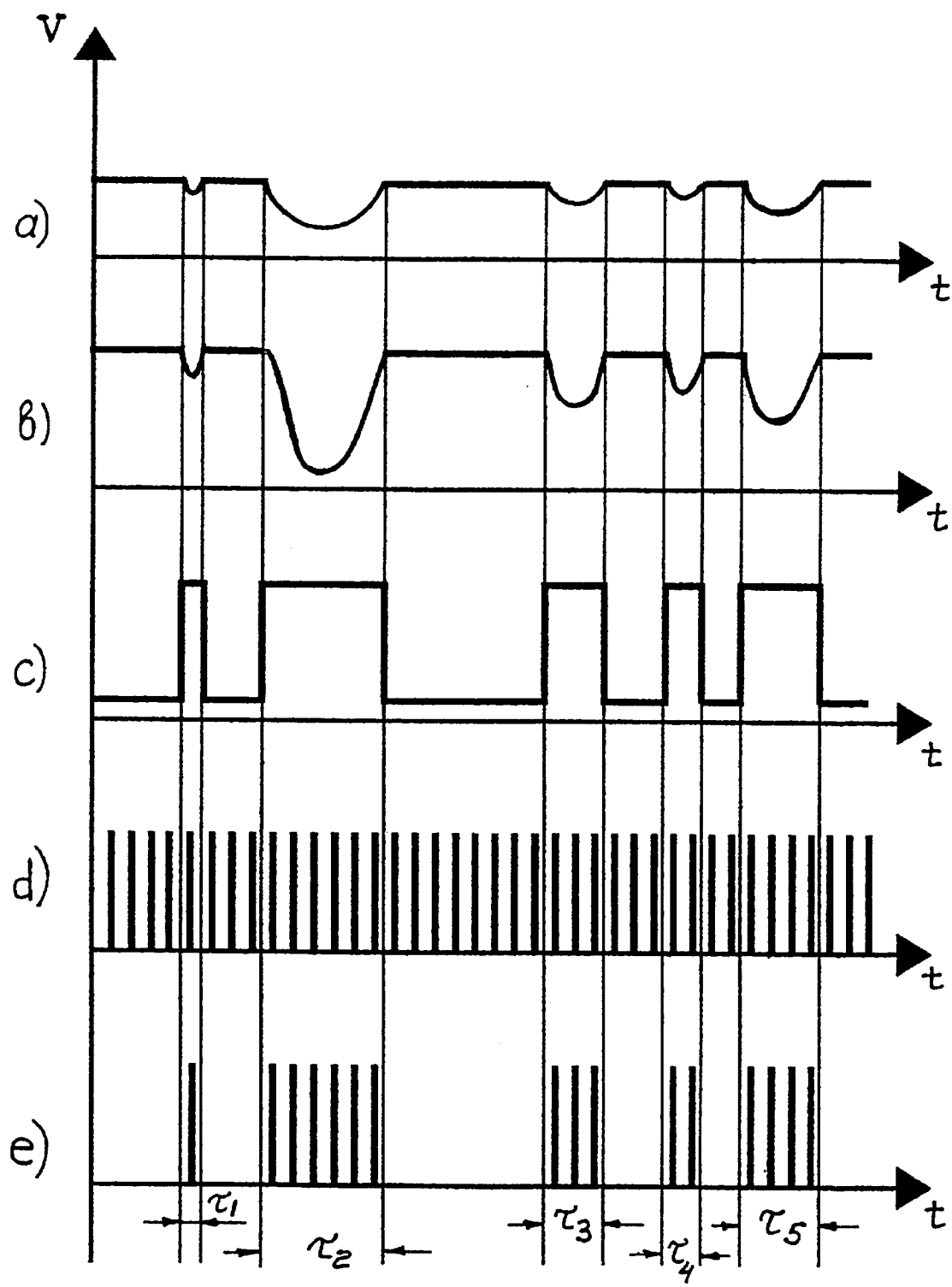
FIG. 10 is a presentation of the signal timing-diagram.

FIG. 10 presents a timing diagram of the signal processing. On this figure $\tau_i$ represents a duration of the pulses, where i=1, 2, 3, . . . .

Figure 11:
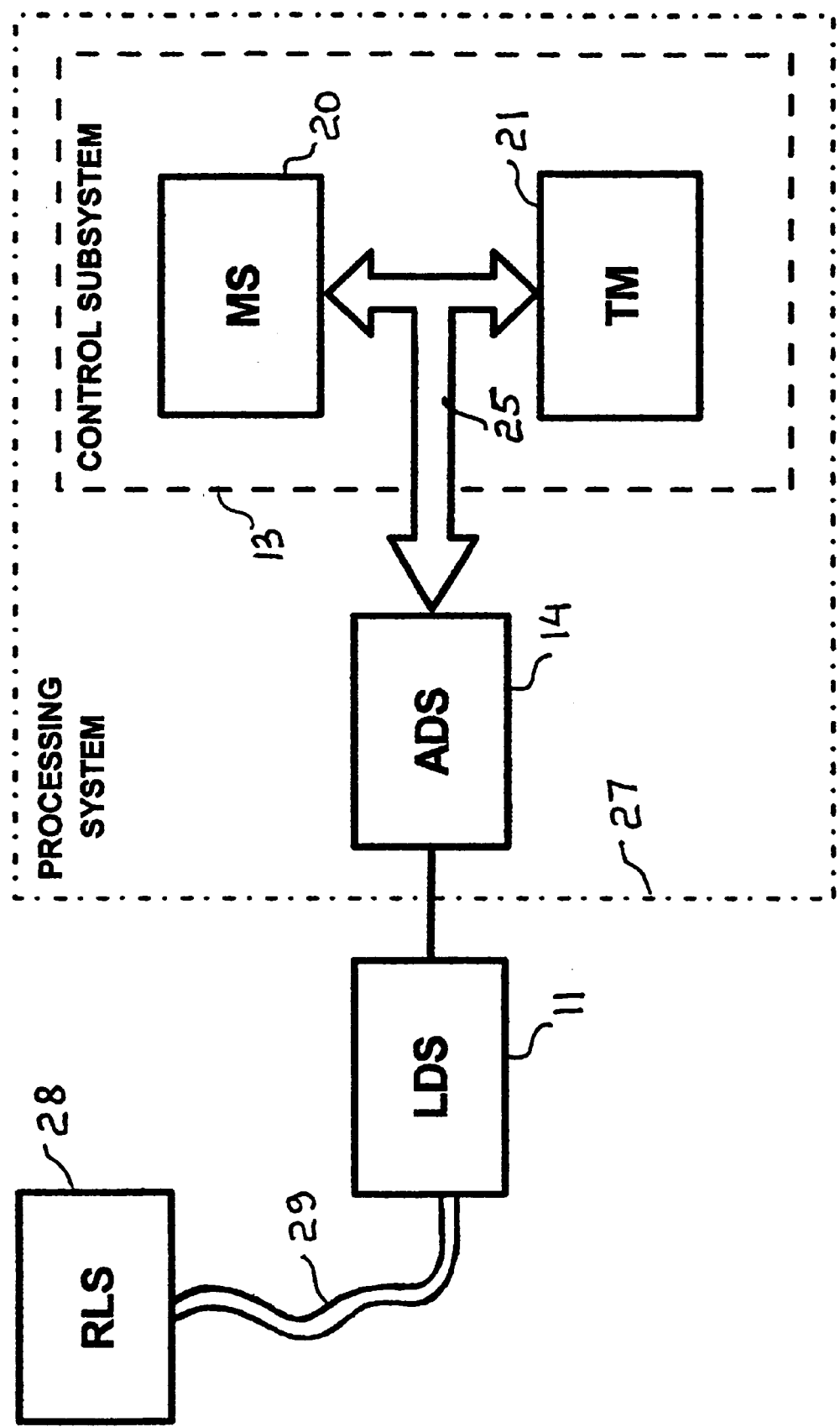
FIG. 11 is a representation of the block-diagram of an improved device with the remote light beam source.

On FIG. 11 is presented a structure of an improved device with a remote light beam source. This device comprises a remote light beam source 28, connected by a fiber optic connecting means 29 to a light detecting system 11, which is electrically connected to a processing system 27, including an analog-digital subsystem 14 and a control subsystem 13, comprising a microprocessor subsystem 20 and a terminal means 21.

An improved device operates as follows. The light or laser beam along axis 2 intersects a particle flow along axis 3 within the particle monitoring regions in the area of a light detection means 4, placed on a light beam axis 2, as shown on FIGS. 6, 7. When the particles of the particle flow intersect the light beam, the intensity of the light beam on the light detection means 4 will be less than at the time when the particles are missing, because the presence of a particle in the light beam is an obstruction for the light in the direction to the light detection means 4. The bigger particle, the less light intensity on the light detection means 4. For other detecting principles (for example, for scattered light collection by lens or mirror collecting system), the light intensity on the light detection means (on the light detector) will be presented when the particles intersect the laser beam. The bigger particle, the higher intensity.

The signals, detected by the light detection means 4, (current signals) follow to the amplifying means 15 of the analog-digital subsystem 14 (FIG. 9) of a processing system 27 of an improved device (see FIG. 8).

An improved timing processing method provides the digital processing of the amplified detected signals (see FIG. 10).

Referring to FIG. 9, the signals amplified by the amplifying means 15 follow to the pulse forming means 24, which converses them to the voltage signal (FIG. 10a), amplifies these voltage signals (FIG. 10b) and forms the digital form pulses shown on FIG. 10c (the digital form pulses can be presented by digital code after an analog-digital converter— not shown). The pulse forming means 24 also comprises an internal interface means (not shown) for comunication by multiplexed bus 25 (or by a data bus and an address bus, which are not shown).

Referring again to FIG. 8 and considering FIG. 9, the signals from the analog-digital subsystem 14 follow by a multiplexed bus 25 to the control subsystem 13. For the timing processing method, mentioned above, the signals (FIG. 10c) from the analog-digital subsystem 14 are strobed by the strobe pulses (see FIG. 10d) in the microprocessor subsystem 20 of the control subsystem 13. The packages of strobe pulses (FIG. 10e) processed by microprocessor subsystem 20 have different durations $\tau_i$ (an appropriate different quantity of strobe pulses). These durations are related to the different sizes of particles, which create different obstructions of the light beam. The quantity of the strobe pulses within the strobe pulse pack contains information about particle size. The more strobe pulses within the strobe pulse pack, the bigger particle size. The quantity of the identical strobe pulse packs (packs, having the same quantity of strobe pulses within) characterizes the quantity of the identical size particles. The higher the frequency of the strobe pulses, the higher precision and of the improved device:

$$S=f(F_P) \qquad [1]$$

and $$S \rightarrow \infty \big|_{F_P \rightarrow \infty}, \qquad [2]$$

where S—a sensitivity;
f—a functional symbol (a function);
$F_P$—a strobe pulses frequency.

The microprocessor subsystem 20 is also connected by the multiplexed bus 25 to a terminal means 21, which can include a display means, a printing means, a compact disk (CD) means.

Referring to FIG. 11, the light beam or laser beam is transferred from a remote light beam source (or remote laser) 28 to the chamber 12 (see FIGS. 6, 7) of a light detecting system 11 by a fiber optic connecting means 29.

CONCLUSION, RAMIFICATION AND SCOPE

Accordingly the reader will see that according to the invention, I have provided a precise and effective methods and devices, which provide counting and measuring of all particles of the assayed air (gas) or liquid. An improved method and device provide authenticity of the real quantity and size of the particles in the assayed mixture of air, gas or liquid, because all particle plurality is considered. Also the improved method and device provide correctness of the resulting information, because the light noise (light background) inside of improved device is eliminated.

While the above description contains many specificities, these should not construed as limitations on the scope of the invention, but as exemplification of the presently-preferred embodiments thereof Many other ramifications are possible within the teaching of the invention. For example, an improved method and device provide authentic counting and measuring of particles, because very precise focusing of the mirrors or optics is not required. The procedure of periodical calibration is much easier for an improved timing processing of the detected signals, because an improved method and device does not require the consideration of the light background, created by non-focused and/or unconsidered scattered light, as it presents in the some known prior art, mentioned above. The improved timing processing of the detected signals provides unlimited sensitivity of the improved device and eliminates necessity of the periodical calibration by manufacturer. Also an improved device uses a single small light detector and can not require a power light beam, as it is necessary for the scattered light detecting system.

Thus, the scope of the invention should be determined by the appended claims and their legal equivalents, and not by examples given.

What is the claimed is:

1. A method for counting and measuring particles illuminated by a light beam and including the steps of:
   providing by a light detecting system an output which is effectively indicative of a size of said particles intersecting said light beam within a particle monitoring region of said light detecting system so that said particles are monitored within said particle monitoring region, and wherein a light, created by the intersection of said particles with said light beam, is proportional to said output;

amplifying said output by an amplifying means;

converting each amplified signal to a digital form pulse having an adequate duration with said output;

forming the strobe pulse packs by strobing of the digital form pulses by strobe pulses of a strobe pulse sequence, and wherein each strobe pulse pack contains at least one strobe pulse of said strobe pulse sequence;

counting a quantity of said strobe pulses within said each strobe pulse pack;

selecting and sorting a plurality of strobe pulse packs by an identical quantity of said strobe pulses within said each strobe pulse pack of said plurality of strobe pulse packs;

counting a quantity of the identical strobe pulse packs.

2. The method of claim 1, wherein said quantity of said strobe pulses within said each strobe pulse pack contains an information about particle size.

3. The method of claim 1, wherein said quantity of said identical strobe pulse packs contains an information about quantity of the identical size particles.

4. A method for counting and measuring a particles illuminated by a light beam and including the steps of:

providing a light detecting system, including a chamber, having a particle monitoring region;

providing a low power light source means forming said light beam directed through said particle monitoring region to a light detection means placed within said chamber on a light beam axis;

providing an intersection of said particles with said light beam at a point within said particle monitoring region so that said particles are monitored in said chamber, and wherein said intersection is occurred at said point located on said light beam axis and substantially in an area of said light detection means between the light source means and said light detection means;

non-optic imaging detecting of a light created by said intersection of said light beam with said particles flowing through said particle monitoring region of said light detecting system, and providing an output which is effectively indicative of a duration of said light proportional to a size of said particles;

amplifying and converting said output to the adequate duration digital form pulses;

processing said digital form pulses by strobing of said digital form pulses by strobe pulses of a strobe pulse sequence, and wherein a quantity of said strobe pulses within each digital form pulse is effectively indicative of the particle size.

5. The method of claim 4, wherein said chamber further is provided with an inside light absorbing black flat coating.

6. A device for counting and measuring particles illuminated by a light beam includes:

a light detecting system, providing a non-optic imaging detection of said particles and comprising a chamber, having a particle monitoring region within which said light beam intersects said particles at a point on a light beam axis;

a low power light source means forming said light beam directed to said particle monitoring region so that said particles are monitored at said point;

a light detection means placed within said chamber on said light beam axis so that said point of said particle monitoring region is located substantially in the light detection means area between the light source means and said light detection means, and wherein said light detecting system provides an output which is effectively indicative of a duration of a light created by the intersection of said light beam with said particles and proportional to a size of said particles, and a processing system providing control functions and processing of said output and comprising an analog-digital subsystem, including an amplifying means, providing an amplification of said output;

a pulse forming means, converting each amplified signal to a digital form pulse with a duration adequate to the duration of the appropriate output signal of said light detecting system;

a control subsystem, including a microprocessor subsystem, providing said control functions and a processing of each said digital form pulse by strobing of said each digital form pulse by strobe pulses of a strobe pulse sequence, creating an appropriate strobe pulse packs containing a quantity of said strobe pulses which is proportional to the size of said particles;

a terminal means connected to said microprocessor subsystem; and wherein said light detecting system is connected to said analog-digital subsystem, which is connected to said control subsystem.

* * * * *

UNITED STATES PATENT AND TRADEMARK OFFICE
CERTIFICATE OF CORRECTION

Page 1 of 2

PATENT NO.        : 6,034,769 C1
APPLICATION NO.   : 90/008385
DATED             : March 7, 2000
INVENTOR(S)       : Yufa It is certified that error appears in the above-identified patent and that said Letters Patent is hereby corrected as shown below:

Column 1,
Line 13, change "lines 40-49" to --39-48--.

Column 1,
Line 24, change "line 50" to --line 49--.

Column 1,
Line 33, change "$t_i$" to --$\tau_i$--.

Column 1,
Line 34, change "quality" to --quantity--.

Column 6, Claim 1,
Line 10, change "output:" to --output;--.

Column 6, Claim 1,
Line 28, change "pack" to --packs--.

Column 7, Claim 4,
Line 4, change
   "having a particle monitoring region; providing a low" to
   --having a particle monitoring region;
 providing a low power light source means forming said light beam--.

Column 7, Claim 4,
Delete Line 5 in its entirety.

Column 7, Claim 4,
Line 20, change "," to --,--.

Signed and Sealed this
Eighteenth Day of September, 2012

David J. Kappos
*Director of the United States Patent and Trademark Office*

Column 7, Claim 4,
Line 21, change "wherein said duration is" to --*wherein said duration is*--.

(12) EX PARTE REEXAMINATION CERTIFICATE (7377th)

United States Patent
Yufa

(10) Number: US 6,034,769 C1
(45) Certificate Issued: Feb. 23, 2010

(54) METHOD AND DEVICE FOR COUNTING AND MEASURING PARTICLES

(75) Inventor: Aleksandr L. Yufa, P.O. Box 1677, Colton, CA (US) 92324

(73) Assignees: Aleksandr L. Yufa, Colton, CA (US); Yelena V. Yufa, Colton, CA (US)

Reexamination Request:
No. 90/008,385, Dec. 21, 2006

Reexamination Certificate for:
| | |
|---|---|
| Patent No.: | 6,034,769 |
| Issued: | Mar. 7, 2000 |
| Appl. No.: | 08/884,680 |
| Filed: | Jun. 27, 1997 |

(51) Int. Cl.
*G01N 15/02* (2006.01)

(52) U.S. Cl. .................... 356/335; 356/336; 356/339; 377/11

(58) Field of Classification Search .................... None
See application file for complete search history.

(56) References Cited

U.S. PATENT DOCUMENTS

| 4,491,926 A | 1/1985 | Okada et al. |
|---|---|---|
| 5,085,500 A | 2/1992 | Blesener |

*Primary Examiner*—B. James Peikari

(57) ABSTRACT

A device for counting and measuring particles provides an analysis of the particle characteristics and includes a processing system 27, comprising a control subsystem 13, including a microprocessor subsystem 20 and a terminal devices 21, an analog-digital subsystem 14, comprising an amplifier 15 and a pulse former 24, and a light detecting system 11, providing particle detection. An improved device determines the size of particles by the quantity of the strobe pulses of the strobe pulse sequence within each strobe pulse pack, formed from the amplified and converted output of the light detecting system 11. The quantity of the identical strobe pulse packs characterizes the quantity of the particles with an appropriate identical size.

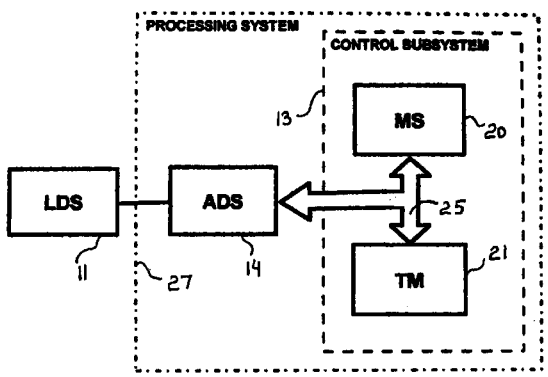

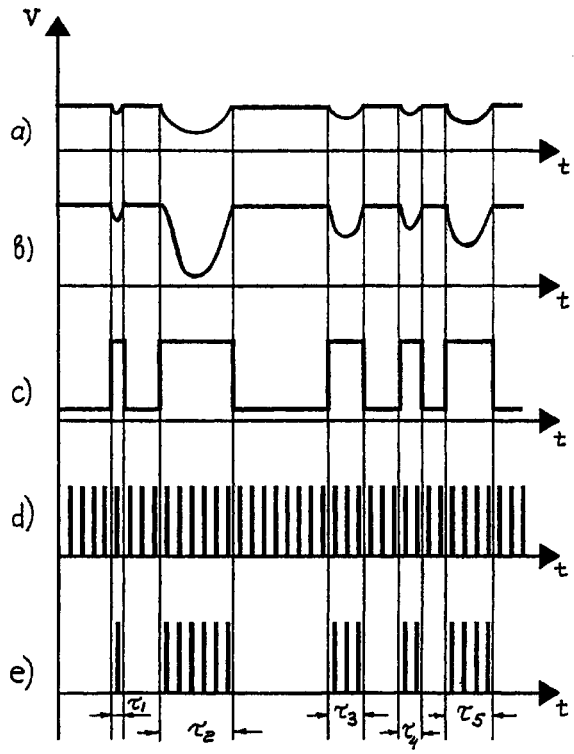

US 6,034,769 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, lines 40–49:

Referring to FIG. 9, the signals amplified by the amplifying means 15 follow to the pulse forming means 24, which[converses] *converts* them to the voltage signal (FIG. 10a), amplifies these voltage signals (FIG. 10b) and forms the digital form pulses shown on FIG. 10c (the digital form pulses can be presented by digital code after an analog-digital converter—not shown). The pulse forming means 24 also comprises an internal interface means (not shown) for communication by multiplexed bus 25 (or by a data bus and an address bus, which are not shown).

Column 5, line 50 to Column 6, line 2:

Referring again to FIG. 8 and considering FIG. 9, the signals from the analog-digital subsystem 14 follow by a multiplexed bus 25 to the control subsystem 13. For the timing processing method, mentioned above, the signals (FIG. 10c) from the analog-digital subsystem 14 are strobed by the strobe pulses (see FIG. 10d) in the microprocessor subsystem 20 of the control subsystem 13. The packages of strobe pulses (FIG. 10e) processed by microprocessor subsystem 20 have different durations $t_i$ (an appropriate different quality of strobe pulses). These durations are related to the different sizes of particles, which create different obstructions of the light beam. The quantity of the strobe pulses within the strobe pulse pack contains information about particle size. The more strobe pulses within the strobe pulse pack, the bigger particle size. The quantity of the identical strobe pulse packs (packs, having the same quantity of strobe pulses within) characterizes the quantity of the identical size particles. The higher the frequency of the strobe pulses, the higher precision [and] of the improved device:

AS A RESULT OF REEXAMINATION, IT HAS BEEN DETERMINED THAT:

Claims 2 and 3 are cancelled.

Claims 1, 4 and 6 are determined to be patentable as amended.

Claim 5, dependent on an amended claim, is determined to be patentable.

1. A method for counting and measuring particles illuminated by a light beam and including the steps of:
providing by a light detecting system an output which is effectively indicative of a size of said particles intersecting said light beam within a particle monitoring region of said light detecting system so that said particles are monitored within said particle monitoring region, and wherein a light, created by [the] *an* intersection of said particles with said light beam, is proportional to said output;
amplifying said output by an amplifying means;
converting each amplified signal to a digital form pulse [having an adequate duration with said output] *without using a reference voltage to convert each said amplified signal, wherein said digital form pulse has a duration which is adequate to a baseline duration of said output of said light detecting system*;
forming [the] strobe pulse packs by strobing of the digital form pulses by strobe pulses of a strobe pulse sequence, and wherein each strobe pulse pack contains at least one strobe pulse of said strobe pulse sequence;
counting a quantity of said strobe pulses within said each strobe pulse pack;
selecting and sorting a plurality of strobe pulse packs by an identical quantity of said strobe pulses within said each strobe pulse pack of said plurality of strobe pulse packs;
counting a quantity of identical strobe pulse pack, *wherein said quantity of said strobe pulses within said each strobe pulse pack contains information about said size of said particles, and wherein said quantity of said identical strobe pulse packs contains information about the quantity of particles of identical sizes*.

4. A method for counting and measuring a particles illuminated by a light beam and including the steps of:
providing a light detecting system, including a chamber, having a particle monitoring region; providing a low power light source means forming said light beam directed through said particle monitoring region to a light detection means placed within said chamber on a light beam axis;
providing an intersection of said particles with said light beam at a point within said particle monitoring region so that said particles are monitored in said chamber, and wherein said intersection is occurred at said point located on said light beam axis and substantially in an area of said light detection means between the light source means and said light detection means;
non-optic imaging detecting of a light created by said intersection of said light beam with said particle flowing through said particle monitoring region of said light detecting system, and providing an output which is effectively indicative of a duration of said light, wherein said duration is proportional to a size of said particles, *and wherein said light, created by said intersection of said light beam with said particles, is the light obstructed by said particles*;
amplifying *said output* and converting [said output] *amplified signals* to [the adequate duration] digital form pulses *without using a reference voltage to convert each of said amplified signals, wherein each of said digital form pulses has a duration which is adequate to a baseline duration of said output of said light detecting system;*
processing said digital form pulses by strobbing of said digital form pulses by strobe pulses of a strobe pulse sequence, and wherein a quantity of said strobe pulses within each digital form pulse is effectively indicative of the particle size.

6. A device for counting and measuring particles illuminated by a light beam includes:
a light detecting system, providing a non-optic imaging detection of said particles and comprising a chamber, having a particle monitoring region within which said light beam intersects said particles at a point on a light beam axis;

a low power light source means forming said light beam directed to said particle monitoring region so that said particles are monitored at said point;

a light detection means placed within said chamber on said light beam axis so that said point of said particle monitoring region is located substantially in [the light detection means area] *an area of said light detection means* between the light source means and said light detection means, [and] wherein said light detecting system provides an output which is effectively indicative of a duration of a light created by [the] *an* intersection of said light beam with said [particles and] *particles, and wherein said duration is* proportional to a size of said particles, and *wherein said light, created by said intersection of said light beam with said particles, is the light obstructed by said particles, and* a processing system providing control functions and processing of said output and comprising an analog-digital subsystem, including an amplifying means, providing an amplification of said output;

a pulse forming means, converting each amplified signal to a digital form pulse [with a duration adequate to the duration of the appropriate output signal] *without using a reference voltage to convert each said amplified signal, wherein said digital form pulse has a duration which is adequate to a baseline duration of said output* of said light detecting system;

a control subsystem, including a microprocessor subsystem, providing said control functions and a processing of each [said] digital form pulse by strobing of said each digital form pulse by strobe pulses of a strobe pulse sequence, creating [an appropriate] strobe pulse packs containing a quantity of said strobe pulses which is proportional to [the] *said* size of said particles;

a terminal means connected to said microprocessor subsystem; and wherein said light detecting system is connected to said analog-digital subsystem, which is connected to said control subsystem.

\* \* \* \* \*

US006034769C2

(12) EX PARTE REEXAMINATION CERTIFICATE (8143rd)
United States Patent
Yufa

(10) Number: US 6,034,769 C2
(45) Certificate Issued: Apr. 5, 2011

(54) METHOD AND DEVICE FOR COUNTING AND MEASURING PARTICLES

(75) Inventor: Aleksandr L. Yufa, Colton, CA (US)

(73) Assignees: Aleksandr L. Yufa, Colton, CA (US); Yelena V. Yufa, Colton, CA (US)

Reexamination Request:
No. 90/009,628, Nov. 2, 2009

Reexamination Certificate for:
Patent No.: 6,034,769
Issued: Mar. 7, 2000
Appl. No.: 08/884,680
Filed: Jun. 27, 1997

Reexamination Certificate C1 6,034,769 issued Feb. 23, 2010

(51) Int. Cl.
G01N 15/02 (2006.01)

(52) U.S. Cl. .................. 356/335; 356/336; 356/339; 377/11

(58) Field of Classification Search .................. None
See application file for complete search history.

(56) References Cited

U.S. PATENT DOCUMENTS 4,491,926 A  1/1985  Okada et al.
5,012,118 A  4/1991  Preikschat et al.
5,084,614 A  1/1992  Berkner Primary Examiner—B. James Peikari

(57) ABSTRACT

A device for counting and measuring particles provides an analysis of the particle characteristics and includes a processing system 27, comprising a control subsystem 13, including a microprocessor subsystem 20 and a terminal devices 21, an analog-digital subsystem 14, comprising an amplifier 15 and a pulse former 24, and a light detecting system 11, providing particle detection. An improved device determines the size of particles by the quantity of the strobe pulses of the strobe pulse sequence within each strobe pulse pack, formed from the amplified and converted output of the light detecting system 11. The quantity of the identical strobe pulse packs characterizes the quantity of the particles with an appropriate identical size.

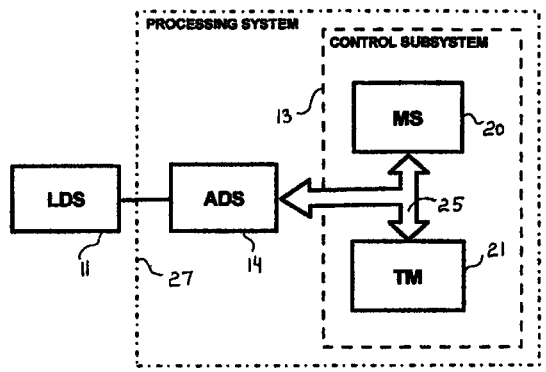

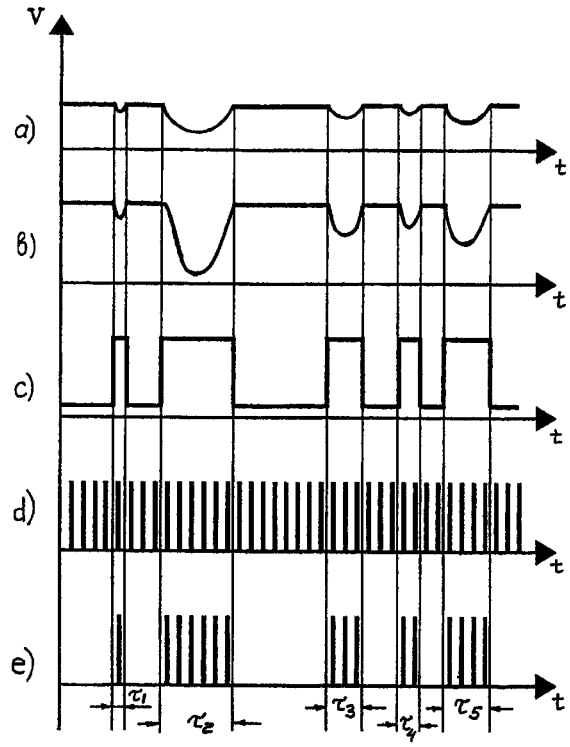

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 4, 5 and 6 is confirmed.

Claims 2 and 3 were previously cancelled.

\* \* \* \* \*

(12) EX PARTE REEXAMINATION CERTIFICATE (9087th)
United States Patent
Yufa

(10) Number: US 6,034,769 C3
(45) Certificate Issued: Jun. 19, 2012

(54) METHOD AND DEVICE FOR COUNTING AND MEASURING PARTICLES

(75) Inventor: Aleksandr L. Yufa, Colton, CA (US)

(73) Assignee: Yelena V. Yufa, Colton, CA (US)

Reexamination Request:
No. 90/012,207, Mar. 23, 2012

Reexamination Certificate for:
Patent No.: 6,034,769
Issued: Mar. 7, 2000
Appl. No.: 08/884,680
Filed: Jun. 27, 1997

Reexamination Certificate C1 6,034,769 issued Feb. 23, 2010

Reexamination Certificate C2 6,034,769 issued Apr. 5, 2011

(51) Int. Cl.
*G01N 15/02* (2006.01)

(52) U.S. Cl. ............... 356/335; 356/336; 356/339; 377/11

(58) Field of Classification Search .................. None
See application file for complete search history.

(56) References Cited

To view the complete listing of prior art documents cited during the proceeding for Reexamination Control Number 90/012,207, please refer to the USPTO's public Patent Application Information Retrieval (PAIR) system under the Display References tab.

*Primary Examiner* — James Menefee

(57) ABSTRACT

A device for counting and measuring particles provides an analysis of the particle characteristics and includes a processing system 27, comprising a control subsystem 13, including a microprocessor subsystem 20 and a terminal devices 21, an analog-digital subsystem 14, comprising an amplifier 15 and a pulse former 24, and a light detecting system 11, providing particle detection. An improved device determines the size of particles by the quantity of the strobe pulses of the strobe pulse sequence within each strobe pulse pack, formed from the amplified and converted output of the light detecting system 11. The quantity of the identical strobe pulse packs characterizes the quantity of the particles with an appropriate identical size.

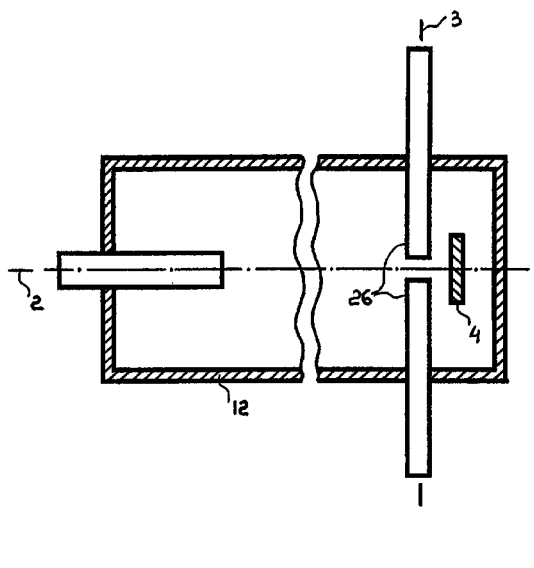
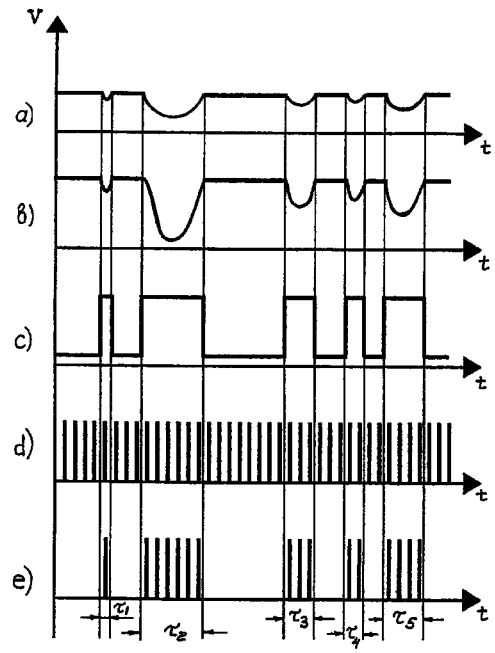

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1 and 4-6 is confirmed.
Claims 2 and 3 were previously cancelled.

\* \* \* \* \*